(12) United States Patent
Ramsay et al.

(10) Patent No.: US 9,743,668 B2
(45) Date of Patent: *Aug. 29, 2017

(54) COMPATIBILIZED ELECTROLYTE FORMULATIONS

(75) Inventors: Julia Lynne Ramsay, Bracknell (GB); David Stock, Bracknell (GB); Gordon Alstair Bell, Bracknell (GB); Claudio Screpanti, Bracknell (GB); Colin Douglas Miln, Greensboro, NC (US); Henry Ebun Agbaje, Greensboro, NC (US); Charles A. Jones, III, Greensboro, NC (US); Ravi Ramachandran, Guelph (CA)

(73) Assignee: Syngenta Crop Protection, LLC, Greensboro, NC (US)

(*) Notice: Subject to any disclaimer, the term of this patent is extended or adjusted under 35 U.S.C. 154(b) by 465 days.

This patent is subject to a terminal disclaimer.

(21) Appl. No.: 13/254,329

(22) PCT Filed: Mar. 4, 2010

(86) PCT No.: PCT/US2010/026202
§ 371 (c)(1),
(2), (4) Date: Jan. 24, 2012

(87) PCT Pub. No.: WO2010/102102
PCT Pub. Date: Sep. 10, 2010

(65) Prior Publication Data
US 2012/0115816 A1   May 10, 2012

Related U.S. Application Data

(60) Provisional application No. 61/158,100, filed on Mar. 6, 2009.

(51) Int. Cl.
| *A01N 57/00* | (2006.01) |
| *A01N 25/00* | (2006.01) |
| *A01N 41/06* | (2006.01) |
| *A01P 17/00* | (2006.01) |
| *A01N 57/20* | (2006.01) |
| *A01N 25/30* | (2006.01) |

(52) U.S. Cl.
CPC .............. *A01N 57/20* (2013.01); *A01N 25/30* (2013.01)

(58) Field of Classification Search
None
See application file for complete search history.

(56) References Cited

U.S. PATENT DOCUMENTS

| 5,565,409 A | 10/1996 | Sato et al. |
| 5,888,934 A | 3/1999 | Townson et al. |
| 2003/0096708 A1* | 5/2003 | Agbaje et al. ............... 504/365 |
| 2003/0104943 A1* | 6/2003 | Lennon et al. ............... 504/206 |
| 2005/0192196 A1* | 9/2005 | Hutton et al. ................ 510/337 |

FOREIGN PATENT DOCUMENTS

| WO | 9909822 | 3/1999 |
| WO | 03094614 | 11/2003 |
| WO | 2004021790 | 3/2004 |

OTHER PUBLICATIONS

Office Action, Notification Date Aug. 15, 2013, U.S. Appl. No. 13/254,354.
Gimenez, A.E., Annual grass control by glyphosate plus bentazon, chlorimuron, fomesafen, or imazethapyr, [online] Weed Technology, 1998, vol. 12, Issue 1 [Retrieved on Aug. 9, 2013]. Retrieved from the internet: <http://www.cabdirect.org/abstracts/19982302747.html;jsessionid=416D20CCB24744240A1DB4C3531DDA6D#>. Abstract.
Mueller, Thomas C., Comparison of Glyphosate Salts (Isopropylamine, Diammonium, and Potassium) and Calcium and Magnesium Concentrations on the Control of Various Weeds, 2006, Weed, Technology, vol. 20, pp. 164-171.

* cited by examiner

*Primary Examiner* — Jeffrey S Lundgren
*Assistant Examiner* — Michael Schmitt
(74) *Attorney, Agent, or Firm* — James Cueva

(57) ABSTRACT

The invention includes aqueous compatibilized pesticidal formulations and methods of making them. In typical embodiments, formulations comprise a first electrolytic pesticide and a second electrolytic pesticide, and about 30 to about 300 g/L of at least one alkyl polyglycoside. The invention also includes methods of preparing pesticidal formulations to increase the concentration of the electrolytic pesticides. The invention also includes storage and transport systems containing formulation embodiments. The invention also includes methods inhibiting pests.

18 Claims, No Drawings

COMPATIBILIZED ELECTROLYTE FORMULATIONS

This application is a 371 of International Application No. PCT/US2010/026202 filed Mar. 4, 2010, which claims priority to U.S. 61/158,100 filed Mar. 6, 2009, the contents of which are incorporated herein by reference.

TECHNICAL FIELD

The present invention relates to aqueous formulations comprising at least two water-soluble electrolytic pesticides at an increased concentration, to the preparation of such formulations using at least one alkyl polyglycoside, and to methods of using such formulations to control unwanted pests.

BACKGROUND

Crop protection agents are often administered in the form of aqueous systems. For example, water-based formulations may be obtained by dissolving, emulsifying and/or suspending pesticidally active ingredients in water prior to application. In order to increase their water solubility, active ingredients are often converted into water-soluble salts by reacting them with a suitable base such as alkali or alkaline-earth metals or water-soluble amines, for example.

Mixes of two or more pesticides are commonly prepared by the grower in a process known as tank mixing to take advantage of the properties of each active ingredient. In tank mixing, typically, two or more concentrated formulations are dissolved, emulsified and/or suspended in a larger volume of a suitable carrier, for example, water. For example, at least two fungicides, at least two herbicides, or at least two insecticides may be tank mixed. In some situations, it may also be desirable to tank mix mixtures of fungicides, herbicides, and/or insecticides. Tank mixes are useful, for example, for control or suppression of a broad spectrum of plant pathogens and for control or suppression of plant pathogens exhibiting resistance or tolerance to a particular pesticide. Tank mixing, however, can often be problematic.

For example, commercially available pesticide concentrates often contain adjuvant systems that are carefully metered and/or specific to particular active ingredients. Tank mixing can increase the amount of adjuvants present in the tank, and/or can increase the effects the adjuvant from one product may have on the activity of the active ingredient of another product. As such, tank mixes of different pesticide concentrates can lead to performance issues, such as increased phytotoxicity to the non-target vegetation, e.g. crops, turf or other desirable plants.

Further, tank mixing can lead to compatibility problems. For example, even at low concentrations, tank mixes of two or more water soluble, electrolytic pesticides, can result in compatibility problems.

When concentrated mixtures of electrolytic pesticides are prepared, formulation compatibility is even more likely to be negatively impacted. For example, when trying to prepare concentrated mixes of two or more electrolytic pesticides for commercial sale, phase separation, formation of solid precipitates, or other formulation failures can occur. Similarly, in some instances, when trying to prepare concentrated tank mixes containing two or more electrolytic pesticides for application, phase separation, formation of solid precipitates, or other mixing problems can occur. Additionally, in some instances, tank mixing may result in crop phytotoxicity and/or pesticide antagonism or reduced efficacy. Further, some commercial mixes may formulate initially, but are not suitable for storage and transport.

Various embodiments of the invention are directed to various combinations of these, and additional, problems.

SUMMARY

Applicants, to their surprise, discovered that compatibilized formulations comprising at least two electrolytic pesticides and at least one alkyl polyglycoside ("APG") could be prepared at significantly higher concentrations than previously possible. Formulations of the instant invention are thus useful as premixes or formulations configured to be diluted to create other application concentrations. Formulations of the instant invention are particularly useful as concentrated premixes. Premixes can be readily formulated with minimal risk of active ingredient incompatibility or antagonism, providing improvements in storage, transport, and application. Formulations of the invention are also particularly useful as components in storage and transport systems. Somewhat similarly, diluted application concentrations formed from premix formulations of the invention are readily prepared with minimal risk of phase separation, precipitation, or antagonism. Further improvements in crop safety compared to tank mixes while maintaining pest, e.g. weed, control are exhibited.

By way of summary, in some embodiments, the invention includes methods for increasing the compatibilized concentration of an electrolytic pesticide mixture (EPM) in an aqueous solution. The EPM comprises at least a first electrolytic pesticide and a second electrolytic pesticide. In one such embodiment, the method comprises adding about 30 to about 300 g/L of at least one alkyl polyglycoside (APG). Typically, methods of the invention allow EPM concentrations to be increased to at least about 85 g a.e./L. More typically, EPM concentrations will be increased to about 100 g a.e./L to about 600 g a.e./L or higher. Throughout the specification, unless otherwise noted, the amounts of EPM are provided on an acid equivalent (a.e.) basis. Concentration is given in weight/volume %, typically as g a.e./L or g/L.

In other embodiments, the invention includes methods of forming a compatibilized concentration of an EPM in an aqueous solution. In one such embodiment, the method comprises adding to a volume of water, about 30 to about 300 g/L of at least one APG; about 75 to about 500 g a.e./L of a first electrolytic pesticide; and about 10 to about 400 g a.e./L of a second electrolytic pesticide.

In other embodiments, the invention includes compatibilized aqueous pesticidal formulations. In one such embodiment, the formulation comprises about 30 to about 300 of at least one APG, and about 85 to about 600 g a.e./L of an electrolytic pesticide mixture (EPM) comprising at least a first electrolytic pesticide and a second electrolytic pesticide.

In other embodiments, the invention includes compatibilized formulations that are apparent based on their compatibilized concentration increase relative to a reference mixture. In one such embodiment, the compatibilized formulation comprises about 30 to about 300 g/L of at least one alkyl polyglycoside and about 85 to about 600 g a.e./L of an EPM at a given ratio. The formulation's EPM concentration at a given ratio is higher than the maximum compatibilized concentration of a similarly formulated reference mixture consisting of the EPM and all other formulation components with the exception that the APG in the formulation of the invention is replaced with an equal amount of water in the reference mixture. In a typical embodiment, the invention's EPM concentration is at least 5% higher than the maximum compatible concentration of the reference mixture. A test for determining the maximum compatibilized concentration of the reference mixture is set forth in the detailed description below.

In other embodiments, the invention includes storage and shipping systems. In one such embodiment, the system comprises a container having a capacity of about 0.1 L to about 200 L. A compatibilized pesticidal formulation according to the invention is substantially filling the container.

In other embodiments, the invention includes methods of inhibiting at least one pest in a crop area. In one such embodiment, the method comprises applying a compatibilized formulation according to the invention to the crop area.

The above summary was intended to summarize certain embodiments of the present invention. Formulations, systems, and methods of the present invention, including additional embodiments, will be set forth in more detail, along with examples demonstrating efficacy, in the figures and detailed description below. It will be apparent, however, that the detailed description is not intended to limit the present invention, the scope of which should be properly determined by the appended claims.

DETAILED DESCRIPTION

The inventors have surprisingly discovered that the addition of an alkyl polyglycoside to formulations comprising at least two electrolytic pesticides, allow for a significant increase in compatibilized formulation concentration. As such, formulations of the instant invention are particularly useful as premixes to be diluted to create other application concentrations. Methods of the invention are also particularly useful for preparing compatibilized pesticide formulations.

"Acid equivalent" or "a.e.", as used herein, means the theoretical yield of parent acid from a pesticidal active ingredient that has been formulated as a derivative (e.g. a salt, and esters, or an amine).

"APG", as used herein, refers to at least one alkyl polyglycoside.

"EPM", as used herein, refers to an electrolytic pesticide mixture.

"Compatibilized", as used herein, means compositions which do not exhibit phase separation under certain conditions. For example, compositions not exhibiting phase separation when stored at 25° C. for one week. Preferably compositions do not exhibit phase separation when stored at 25° C. for one week and do not form crystals of the active herbicidal ingredient when stored at −5° C. for 24 hours. Cloud Point, as described herein, can also be used to demonstrate high temperature storage stability.

"Electrolytic", as used herein, means capable of creating an aqueous solution containing free ions that behaves as an electrically conductive medium.

"Water-soluble", as used herein, means having a solubility in deionized water at 20° C. sufficient to enable the water-soluble agrochemical electrolyte to be dissolved completely in the aqueous phase of a composition of the invention at the desired concentration. Preferred water-soluble active ingredients useful in the present invention have a solubility in deionized water at 20° C. of not less than about 10,000 mg/l, more preferably not less than about 100,000 mg/l. Where an active ingredient compound is referred to herein as being water-soluble, but the compound itself is known not to be water-soluble, it will be understood that the reference applies to water-soluble derivatives, more particularly water-soluble salts, of the compound.

In some embodiments, the invention includes methods for increasing the compatibilized concentration of an electrolytic pesticide mixture (EPM) in an aqueous solution. The EPM usually comprises at least a first electrolytic pesticide and a second electrolytic pesticide, and in some embodiments, it may include additional electrolytic pesticides, e.g., a third, fourth, fifth, or sixth, for example.

The method comprises adding at least one APG in an amount sufficient to increase the compatibilized concentration of the EPM. Typical APG amounts useful for increasing the compatibilized concentration are about 30 to about 300 g/L. More typically, APG is added at about 4% to about 20%.

In typical embodiments, the EPM concentration is increased by at least about 10 g a.e./L, preferably by at least 50 g a.e./L above the EPM concentration of a reference mixture not containing APG. In many embodiments, the increase in EPM concentration is much greater, for example, in some embodiments, the EPM concentration is at least twice the EPM concentration of the reference mixture.

Electrolytic pesticides in the EPM are inclusive of electrolytic herbicides, electrolytic fungicides, and electrolytic insecticides. Typically, the pesticides in the EPM will include pesticides chosen from a water-soluble salt of acifluorfen, acrolein, aminopyralid, amitrole, asulam, benazolin, bentazone, bialaphos, bromacil, bromoxynil-potassium, chloramben, chloroacetic acid, clopyralid, 2,4-D, 2,4-DB, dalapon, dicamba, dichlorprop difenzoquat, endothall, fenac, fenoxaprop, flamprop, flumiclorac, fluoroglycofen, flupropanate, fomesafen, fosamine, glufosinate, glyphosate, imidazolinones such as imazameth, imazamethabenz, imazamox, imazapic, imazapyr, imazaquin and imazethapyr, ioxynil, MCPA, MCPB, mecoprop, methylarsonic acid, naptalam, nonanoic acid, phenoxy-type herbicides, picloram, quinclorac, sulfamic acid, 2,3,6-TBA, triclopyr, and a compound of the formula

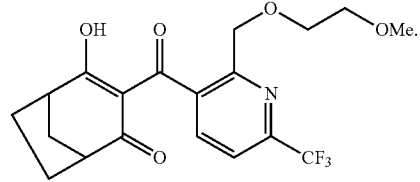 [SMILES: COCCOCc1nc(C(F)(F)F)ccc1C(=O)C1=C(O)C2CCC(C2)C1=O]

Phenoxy-type herbicides, as used herein, are salt-forming herbicides having a mode of action and/or selectivity towards broadleaved plant species that is characteristic of phenoxy herbicides or similar thereto and include phenoxy herbicides. Phenoxy herbicides are salt-forming herbicides that include without limitation phenoxyacetic acids such as 4-CPA; 2,4-D; 3,4-DA; MCPA and 2,4,5-T; phenoxypropanoic acids such as cloprop; 4-CPP; dichlorprop; 3,4-DP; fenoprop and mecoprop; and phenoxybutanoic acids such as 4-CPB; 2,4-DB; 3,4-DB; MCPB and 2,4,5-TB; including enantiomers (e.g., dichlorprop-P and mecoprop-P) as well as racemates thereof.

Salt-forming herbicides that are not phenoxy herbicides in a strict sense but fall within the above definition of 'phenoxy-type' herbicides include without limitation benzoic acids such as chloramben; dicamba; 2,3,6-TBA and tricamba; picolinic acids such as aminopyralid; clopyralid and picloram; and pyridinyloxyacetic acids such as triclopyr; including enantiomers as well as racemates thereof.

Phenoxy-type herbicides in the form of any agriculturally acceptable salt thereof, including potassium, sodium, ammonium and organic ammonium (more particularly low molecular weight organic ammonium) salts can be used in the present invention. Low molecular weight organic ammonium salts include without limitation methylammonium, dimethylammonium, diglycolammonium, propylammonium (n-propylammonium and isopropylammonium), mono-, di- and triethanolammonium salts.

Typical electrolytes include glyphosate (N-phosphonomethylglycine), which is commonly used in the form of its water-soluble salts such as potassium, trimethylsulphonium, isopropylamine, sodium, ammonium, diammonium, dimethylamine and triethanolamine salts including mixtures of two or more of these salts, fomesafen which is commonly used in the form of its water-soluble sodium salt, glufosinate which is commonly used in the form of its water-soluble ammonium salt, dicamba which is commonly used in the form of its diglycolamine, dimethlyammonium, isopropylamine, potassium or sodium salts, and bentazone which is commonly used in the form of its sodium salt.

As needed, pesticides may be converted into water-soluble salts by reacting them with a suitable base such as alkali or alkaline-earth metals or water-soluble amines. Salts of the pesticidally active ingredients are relatively easy to manufacture, generally requiring only mixing of the appropriate active acid and a chosen base. Typical salt forms include potassium, trimethylsulphonium, isopropylamine, sodium, dimethylamine, triethanolamine, diammonium and ammonium. Exemplary salts include, for example, glyphosate-diammonium, glyphosate-potassium, glyphosate-isopropylamine, glufosinate-ammonium, dicamba-diglycolamine, dicamba-sodium, dicamba-potassium, dicamba-dimethylammonium, bentazone-sodium, and fomesafen-sodium.

The alkyl polyglycoside (APG) has formula (I):

$$R_1O(R_2O)_b(Z)_a \quad (I)$$

$R_1$ is a straight or branched chain alkyl or alkenyl group having from about 4 to about 30 carbon atoms. $R_1$ is typically a straight or branched chain $C_{4-22}$ alkyl or alkenyl group, more typically a $C_{8-11}$ alkyl group. $R_2$ is an alkylene having from about 2 to about 4 carbon atoms. $R_2$ is typically ethylene or propylene, more preferably ethylene. b is 0 to about 100. b is preferably 0 to about 12, more preferably 0. Z is a saccharide residue having about 5 to about 6 carbon atoms. Z may be glucose, mannose, fructose, galasctose, talose, gulose, altrose, allose, apiose, gallose, idose, ribose, arabinose, xylose, lyxose, or a mixture thereof. Z is typically glucose. 'a' is an integer from 1 to about 6, preferably from 1 to about 3, more preferably from 1 to about 2.

Typical compounds of formula (I) are compounds of formula (II):

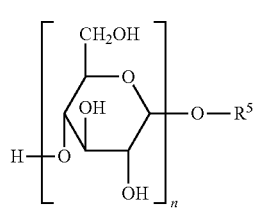

where n is the degree of polymerization and is from 1 to 3, preferably about 1 to about 2, and $R^5$ is a branched or straight chain alkyl group having from 4 to 18 carbon atoms or a mixture of alkyl groups having from 4 to 18 carbon atoms. Most typically, the alkyl polyglycoside comprises an alkyl group containing 8-10 carbon atoms and has an average degree of polymerization of 1.7; an alkyl group containing 9-11 carbon atoms and has an average degree of polymerization of 1.3 to 1.6; or a mixture thereof. APG also includes embodiments, such as those described above, which have been anionically or cationically modified.

Exemplary alkyl polyglycosides include APG® 325 (Cognis Corporation, Cincinnati, Ohio) (an alkyl polyglycoside in which the alkyl group contains 9 to 11 carbon atoms and has an average degree of polymerization of 1.6), PLANTAREN® 2000 (Cognis Corporation, Cincinnati, Ohio) (an alkyl polyglycoside in which the alkyl group contains 8 to 16 carbon atoms and has an average degree of polymerization of 1.4), PLANTAREN® 1300 (Cognis Corporation, Cincinnati, Ohio) (an alkyl polyglycoside in which the alkyl group contains 12 to 16 carbon atoms and has an average degree of polymerization of 1.6), AGNIQUE® PG 8107 (Cognis Corporation, Cincinnati, Ohio) (an alkyl polyglycoside in which the alkyl group contains 8 to 10 carbon atoms and has an average degree of polymerization of 1.7), AGNIQUE® PG 9116 (Cognis Corporation, Cincinnati, Ohio) (an alkyl polyglycoside in which the alkyl group contains 9 to 11 carbon atoms and has an average degree of polymerization of 1.6) and AGNIQUE® PG 8105 (Cognis Corporation, Cincinnati, Ohio) (an alkyl polyglycoside in which the alkyl group contains 8 to 10 carbon atoms and has an average degree of polymerization of 1.5).

The method may further comprise adding, by mass/volume %, about 1% to about 15% of a hydrotrope, Typical hydrotropes include salts of xylene sulphonic acid, salts of cumene sulphonic acid or salts of toluene sulphonic acid. More typically, the hydrotrope will be sodium xylene sulphonate (SXS). In some embodiments, hydrotropes may be desirable to further increase concentration loading. Additionally, hydrotropes may also be desirable for lowering viscosity for improved handling, dilution, and application.

The formulations may include other components such as adjuvants, surfactants, solvents, antisettling agents, antifreeze agents, antifoam agents, preservatives and sequestrants.

Suitable surfactants include those known in the art, for example, anionic surfactants such as alkybenzene sulfonates, alkyl naphthalene sulfonates, alcohol sulfonates, ether sulfates, alkyl sulfosuccinates, sulfonated naphthalene/formaldehyde condensates, lignosulfonates, polycarboxylates, olefin sulfonates, phosphate ethoxylates, tristyrylphenol phosphates and sulfates and taurates; non-ionic surfactants such as alkylphenol ethoxylates, tristyrylphenol ethoxylates, alcohol ethoxylates, alkyl ester ethoxylates, aliphatic acid ethoxylates, sorbitan esters and ethoxylates, castor oil ethoxylates, amine ethoxylates, polymeric surfactants, for example block copolymers and comb/graft copolymers, organosilicones and cetylenic diols; cationic surfactants such as quaternary ammonium compounds, amine salts, amine oxides and amine ethoxylates; and amphoteric surfactants. In an embodiment, the presence of the APG allows for an increase in the amount of surfactant that can be incorporated into the compatibilized concentrate composition compared to a similarly formulated composition except wherein the amount of APG has been replaced with water.

Other embodiments of the invention include methods of forming a compatibilized concentration of an EPM in an aqueous solution. In one such embodiment, the method comprises adding to a volume of water about 30 to about 300 g/L of at least one APG; about 75 to about 500 g a.e/L of a first electrolytic pesticide; and about 10 to about 400 g a.e./L of a second electrolytic pesticide. More typically, the first electrolytic pesticide is added at an amount chosen from about 100, 125, 150, 175, 200, 225, 250, 275 and 300 g a.e./L to about 500 g a.e./L. The second electrolytic pesticide is typically added at an amount chosen from about 10, 25, 50, 75, 100, 125 and 150 g a.e./L to about 400 g a.e./L. Most typically, the first electrolytic pesticide is added at about 125 to about 400 g a.e./L and the second electrolytic pesticide is added at about 25 to about 400 g a.e./L.

For the various formulation embodiments and methods of making formulations, the EPM and APG are as described above.

Additional embodiments of the invention include compatibilized aqueous pesticidal formulations. In one such embodiment, the formulation comprises about 30 to about 300 g/L of at least one APG, and about 85 to about 600 g a.e./L of an EPM comprising at least a first electrolytic pesticide and a second electrolytic pesticide. In typical embodiments, the EPM is present at about 125 to about 500 g a.e./L, at about 150 to about 500 g a.e./L, at about 175 to about 500 g a.e./L, at about 200 to about 500 g a.e./L, and at about 250 to about 500 g a.e./L.

In some embodiments, formulations of the invention are readily described by the improvement they provide in the art. For example, in one embodiment, the invention includes a compatibilized aqueous pesticidal formulation comprising about 50 to about 300 g/L of at least one alkyl polyglycoside, and about 50 to about 500 g a.e./L of an EPM at a given ratio. Common EPM ratios include, for example, 9:1, 6:1, 3:1, 2:1, 1:1, 1:2, 1:3, 1:6 and 1:9.

In one embodiment, the first electrolytic pesticide comprises salts of glyphosate or glufosinate. In another embodiment, the first electrolytic pesticide comprises salts of glyphosate or glufosinate and the second electrolytic pesticide comprises at least one member selected from the group consisting of salts of 2,4-D; dicamba and fomesafen. In one embodiment, the first electrolytic pesticide comprises salts of glyphosate, preferably diammonium, isopropylamine or potassium salts of glyphosate; and the second electrolytic pesticide comprises at least one member selected from isopropyamine or diglycolamine salts of dicamba and sodium salts of fomesafen.

In one embodiment, the EPM concentration at the given ratio is higher than the maximum compatibilized concentration of a reference mixture consisting of the EPM and water. The reference mixture's EPM has the same pesticide ratio as the invention formulation's EPM. The invention's compatibilized formulation may be significantly higher than that of the reference mixture. For example, the invention includes EPM concentration improvements of at least 10 g a.e./L; at least 20 g a.e./L; at least 30 g a.e./L; at least 40 g a.e./L; at least 50 g a.e./L; at least 60 g a.e./L; at least 70 g a.e./L; at least 80 g a.e./L; at least 90 g a.e./L; at least 100 g a.e./L; at least 110 g a.e./L; at least 120 g a.e./L; at least 130 g a.e./L; at least 140 g a.e./L; at least 150 g a.e./L; at least 160 g a.e./L; at least 170 g a.e./L; at least 180 g a.e./L; at least 190 g a.e./L; and at least 200 g a.e./L relative to the maximum compatibilized concentration of a similarly formulated reference mixture consisting of the EPM and all other formulation components with the exception that the APG in the formulation of the invention is replaced with an equal amount of water in the reference mixture. Typically, the invention's EPM concentration is at least 10 g a.e./L, preferably at least 50 g a.e./L higher than the reference mixture's maximum compatibilized concentration, and in some embodiments, the invention's EPM concentration is at least 100 g a.e./L higher than the reference mixture's maximum compatibilized concentration.

The following Test is one means of determining the maximum compatibilized concentration of the reference mixture, consisting of the EPM and water.

Test

An arbitrary test mass of the EPM, at the given ratio, is added to approximately 0.5 L of water with constant stirring at room temperature. The solution is brought to 1 L and stirred for an additional 30 minutes to create a test solution.

Those of ordinary skill in the art will recognize that the selection of the arbitrary test mass will be based on the concentration of the invention formulation. For example, if the compatibilized invention formulation has a 400 g a.e./L EPM concentration in a 3:1 ratio (300 g/L pesticide A+100 g/L pesticide B), an arbitrary test mass might include: (1) 150 g pesticide A+50 g pesticide B; (2) 180 g pesticide A+60 g pesticide B; or (3) 210 g pesticide A+70 g pesticide B.

The test solution is covered and stored at room temperature for one week and then moved to −5° C. for 24 hours (the test period). If any phase separation or crystallization is observed during the test period, the test solution is deemed incompatible. If no phase separation or crystallization is observed during the test period, the test solution is deemed compatible.

If the first test solution is deemed compatible, a new test solution is formed with an increased EPM concentration and evaluated as above for compatibility. If the first test solution is deemed incompatible, a new test solution is prepared with a decreased EPM concentration and evaluated as above for compatibility. Of course, these tests can be performed sequentially or simultaneously.

New test solutions are prepared until the maximum compatibilized concentration±5 g/l of the reference mixture is determined. By way of example, if Test Solution #1 is deemed compatible at a concentration of 160 g a.e./L EPM (120 g/L Pesticide A+40 g/L Pesticide B) and Test Solution #2 is deemed incompatible at a concentration of 164 g a.e./L EPM (123 g/L Pesticide A+41 g/L Pesticide B), then the reference mixture's maximum compatibilized concentration would be 160 g a.e./L.

For aqueous solution concentrates, high temperature storage stability is often indicated by a Cloud Point of about 50° C. or more. Cloud Point of a composition is normally determined by heating a composition from 25° C., with agitation, while its temperature is continuously monitored, and recording the temperature at which cloudiness is detected. A temperature reading taken when the solution clears is a measure of Cloud Point. A Cloud Point of 50° C. or more is acceptable for most commercial purposes for an aqueous concentrate. Ideally the Cloud Point should be 60° C. or more, and the composition should withstand temperatures as low as about −10° C. for up to about 7 days without crystal growth.

In other embodiments, the invention includes storage and shipping systems. Typical storage and shipping systems comprise a container ranging in capacity from about 0.1 L to about 200 L and a compatibilized aqueous pesticidal formulation located in the container. Typically the formulation will be concentrated. The container may include the standard 2.5 gallon (9.46 L) containers widely used in the United States, which typically take the form of jugs or flasks with a replaceable screw-cap. These containers are generally designed for single use and are typically not returned to the supplier when empty, instead being disposed of by the end user in accordance with local agricultural chemical container disposal guidelines, procedures, regulations or laws. Commonly, a plurality of these small containers are packaged within a single box and a plurality of such boxes are shipped on a pallet. During shipment, the small containers (usually within boxes on pallets) can be disposed in an enclosed volume such as provided by a rail boxcar or road truck, the hold of a ship or aircraft, or a modular box container adapted for transport by road, rail and water. Larger single-use containers, ranging in capacity up to about 200 L, for example about 50 L to about 200 L, are commonly in the form of drums, and can be shipped in an enclosed volume as described above, one or more per pallet or unpalleted.

Formulations of the invention also can be distributed in a large refillable container sometimes known as a bulk or minibulk tank, which typically has an integral pump or connector for an external pump to permit transfer of liquid. Bulk or minibulk tanks having a capacity of about 200 to about 2000 liters or more are typically returned to the supplier when empty and are commonly shipped on a pallet.

A compatibilized pesticidal formulation according to the invention is substantially filling the container.

Commercially available pesticide concentrates often contain adjuvant systems that are carefully metered and/or specific to particular active ingredients. Tank mixing can increase the amount of adjuvants present in the tank, and/or can increase the effects the adjuvant from one product may have on the activity of the active ingredient of another product. As such, tank mixes of different pesticide concentrates can lead to performance issues, such as increased phytotoxicity to the non-target vegetation, e.g. crops, turf or other desirable plants. In other embodiments, the invention includes methods for improving crop safety compared to tank mixes of formulations, for example commercially available formulations, of the individual active ingredients, preferably while maintaining similar levels of pest, e.g. weed, control.

In other embodiments, the invention includes methods of inhibiting at least one pest in a crop area. Examples of pests include insects, fungi, and weeds. More typically, examples of pests include insects, fungi, and weeds that decrease crop yield. Inhibition includes suppression, and/or prevention, and/or any negative impact on pest fitness.

Preferred crops of useful plants include canola, cereals such as barley, oats, rye and wheat, cotton, maize, soya, sugar beets, sugar cane, fruits, berries, nuts, vegetables, flowers, trees, shrubs and turf.

Crops are to be understood as also including those crops which have been rendered tolerant to herbicides or classes of herbicides (e.g. ALS-, GS-, EPSPS-, PPO-, ACCase, Auxin- and HPPD-inhibitors) by conventional methods of breeding or by genetic engineering. An example of a crop that has been rendered tolerant to imidazolinones, e.g. imazamox, by conventional methods of breeding is Clearfield® summer rape (canola)(BASF). Examples of crops that have been rendered tolerant to herbicides by genetic engineering methods include e.g. glyphosate- and glufosinate-resistant maize varieties commercially available under the trade names RoundupReady® (Monsanto) and LibertyLink® (Bayer CropScience).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavor).

Other useful plants include turf grass for example in golf-courses, lawns, parks and roadsides, or grown commercially for sod, and ornamental plants such as flowers or bushes.

Crop areas are areas of land on which the cultivated plants are already growing or in which the seeds of those cultivated plants have been sown, and also areas of land on which it is intended to grow those cultivated plants.

In one such embodiment, the method comprises applying a compatibilized formulation according to the invention to the crop area. The method may also include diluting the formulation prior to application. In one embodiment, the compositions are applied postemergence to the crops.

In one embodiment, the composition comprises at least one salt of glyphosate, at least one salt of fomesafen and APG and is applied postemergence to glyphosate tolerant crops, preferably glyphosate tolerant cotton or soybeans.

In one embodiment, the composition comprises at least one salt of glyphosate, at least one salt of dicamba and APG and is applied postemergence to glyphosate tolerant crops, preferably glyphosate tolerant corn or to crops that have been transgenically modified to be tolerant to glyphosate and dicamba, preferably soybeans and cotton.

Advantages of the invention are further illustrated in the examples below.

Examples

In order that those skilled in the art will be better able to practice the invention, the following examples are given by way of illustration and not by way of limitation. In the following examples, as well as elsewhere in the specification and claims, temperatures are in degrees Celsius, the pressure is atmospheric and all parts are by weight %, or weight/volume %, unless otherwise clearly indicated.

Table 1 illustrates diammonium glyphosate normal compatibility profile with sodium fomesafen.

TABLE 1

| Glyphosate:fomesafen ratio | Concentrations giving initial compatibility (one phase solution) Concentrations in g a.e./L | Concentrations giving incompatibility (two phases) Concentrations in g a.e./L |
|---|---|---|
| 9:1** | <=137 g a.e./L gly + 15 g a.e./L fom** | >=155 g a.e./L gly + 17 g a.e./L fom** |

TABLE 1-continued

| Glyphosate:fomesafen ratio | Concentrations giving initial compatibility (one phase solution) Concentrations in g a.e./L | Concentrations giving incompatibility (two phases) Concentrations in g a.e./L |
|---|---|---|
| 6:1** | <=133 g a.e./L gly + 22 g a.e./L fom** | >=150 g a.e./L gly + 25 g a.e./L fom** |
| 3:1 | <=135 g a.e./L gly + 45 g a.e./L fom | >=155 g a.e./L gly + 52 g a.e./L fom |
| 1:1 | <=117 g a.e./L gly + 117 g a.e./L fom | >=140 g a.e./L gly + 140 g a.e./L fom |
| 1:2 | <=110 g a.e./L gly + 220 g a.e./L fom | >=120 g a.e./L gly + 240 g a.e./L fom |
| 1:3 | <=87 g a.e./L gly + 262 g a.e./L fom | |

**formation of a white crystalline precipitate after 24 hours at ambient temperature Table 1 also illustrates concentration ranges for different mixture ratios over which incompatibility arises. For the 9:1 ratio, the mixture becomes incompatible at a glyphosate concentration somewhere between 137 g a.e./L and 155 g a.e./L. For the 6:1 ratio, the mixture becomes incompatible at a glyphosate concentration somewhere between 133 g a.e./L and 150 g a.e./L. For the 3:1 ratio, the mixture becomes incompatible at a glyphosate concentration somewhere between 135 g a.e./L and 155 g a.e./L. For the 1:1 ratio, the mixture becomes incompatible at a glyphosate concentration somewhere between 117 g a.e./L and 140 g a.e./L.

Table 2 illustrates the diammonium glyphosate-sodium fomesafen compatibility achieved by the use of APG.

TABLE 2

| 9:1 Ratio | 3:1 Ratio | 1:2 Ratio |
|---|---|---|
| 315 g a.e./L diammonium glyphosate | 270 g a.e./L diammonium glyphosate | 150 g a.e./L diammonium glyphosate |
| 35 g a.e./L sodium fomesafen | 90 g a.e./L sodium fomesafen | 300 g a.e./L sodium fomesafen |
| 214 g/L Agnique PG 8107 | 214 g/L Agnique PG 8107 | 214 g/L Agnique PG 8107 |
| Water to 1 l | Water to 1 l | Water to 1 l |
| Clear brown solution* | Clear brown solution | Clear brown solution |

*additionally no white precipitate forms with the 9:1 ratio after 24 hours at ambient temperature Surprisingly, for each mixture ratio, significantly higher compatibilized glyphosate concentrations were formulated relative to the formulations in Table 1.

Table 3 illustrates additional compatible formulations after four weeks at ambient temperature.

TABLE 3

| 2:1 Ratio | 2:1 Ratio | 3:1 Ratio | 3:1 Ratio | 4:1 Ratio | 4:1 Ratio |
|---|---|---|---|---|---|
| 240 g a.e./L diammonium glyphosate | 240 g a.e./L diammonium glyphosate | 280 g a.e./L diammonium glyphosate | 280 g a.e./L diammonium glyphosate | 320 g a.e./L diammonium glyphosate | 320 g a.e./L diammonium glyphosate |
| 120 g a.e./L ammonium fomesafen | 120 g a.e./L sodium fomesafen | 93 g a.e./L ammonium fomesafen | 93 g a.e./L sodium fomesafen | 80 g a.e./L ammonium fomesafen | 80 g a.e./L sodium fomesafen |
| 214 g/l Agnique PG 8107 | 214 g/l Agnique PG 8107 | 214 g/l Agnique PG 8107 | 214 g/l Agnique PG 8107 | 214 g/l Agnique PG 8107 | 214 g/l Agnique PG 8107 |
| Clear solution | Clear solution | Clear solution | Clear solution | Clear solution | Clear solution |

Table 4 illustrates additional compatible formulations after four weeks at −5° C.

TABLE 4

| 2:1 Ratio | 2:1 Ratio | 3:1 Ratio | 3:1 Ratio | 4:1 Ratio | 4:1 Ratio |
|---|---|---|---|---|---|
| 210 g a.e./L diammonium glyphosate | 240 g a.e./L diammonium glyphosate | 210 g a.e./L diammonium glyphosate | 240 g a.e./L diammonium glyphosate | 210 g a.e./L diammonium glyphosate | 280 g a.e./L diammonium glyphosate |
| 105 g a.e./L ammonium fomesafen | 120 g a.e./L sodium fomesafen | 70 g a.e./L ammonium fomesafen | 80 g a.e./L sodium fomesafen | 53 g a.e./L ammonium fomesafen | 70 g a.e./L sodium fomesafen |

TABLE 4-continued

| 2:1 Ratio | 2:1 Ratio | 3:1 Ratio | 3:1 Ratio | 4:1 Ratio | 4:1 Ratio |
|---|---|---|---|---|---|
| 214 g/l Agnique PG 8107 | 214 g/l Agnique PG 8107 | 214 g/l Agnique PG 8107 | 214 g/l Agnique PG 8107 | 214 g/l Agnique PG 8107 | 214 g/l Agnique PG 8107 |
| Clear solution | Clear solution | Clear solution | Clear solution | Clear solution | Clear solution |

Table 5 illustrates ammonium glufosinate's incompatibility with sodium fomesafen in the absence of an alkyl polyglycoside, and one example of the concentrated compatibility achievable by the instant invention.

TABLE 5

| Glufosinate NH4:fomesafen Na 3:1 | Glufosinate NH4:fomesafen Na 3:1 + APG (Agnique PG 8107) |
|---|---|
| 300 g a.e./L glufosinate ammonium | 300 g a.e./L glufosinate ammonium |
| 100 g a.e./L fomesafen sodium | 100 g a.e./L fomesafen sodium |
| Water to 1 L | 214 g/L Agnique PG 8107 |
|  | Water to 1 L |
| Result - incompatible, two liquid phases present, bottom fomesafen liquid phase forms solid precipitate with time | Result - clear brown solution |

Compositions containing Dicamba-IPA and Glyphosate-IPA salts were prepared with and without alkylpolyglucosides (APG's). Preparation of Sample No 4 is described below. Preparation of all samples in Table 6 followed a similar methodology.

Water (18.20 g, tap water) was added to a vessel under agitation followed by addition of an aqueous solution of IPA-glyphosate (34.78 g, 46% ae) and an aqueous solution of IPA-Dicamba (34.92 g, 22.9% ae). The resulting solution was agitated until homogenous and was followed by addition of propylene glycol (PG) (5.71 g), antifoam (Agnique DFM 114S, 0.114 g), Agnique PG8107 alkylpolyglucoside (APG) (6.86 g) and finally Toximul TA20 (13.71 g). The final solution was agitated until a transparent homogeneous solution was obtained.

The Cloud Point of this sample was then measured by partially submersing the glass jar containing the sample into a container of water which was then subjected to controlled heating (~1° C./minute) using a hot plate (Fisher Scientific Isotemp). A magnetic stirrer was used to stir the sample during the heating process and a thermometer placed in contact with the sample measured the sample temperature. The temperature at which the sample became cloudy was then recorded as the Cloud Point. Typically a temperature range best described the appearance of cloudiness.

| | Wt (g) | % w/w |
|---|---|---|
| Glyphosate-IPA | 34.78 | 14 (AE % w/w) |
| Dicamba-IPA | 34.92 | 7 (AE % w/w) |
| APG | 6.86 | 6.0 |
| Toximul TA20 | 13.71 | 12.0 |
| Propylene glycol | 5.71 | 5.0 |
| Agnique DFM114FS | 0.11 | 0.1 |
| Water | 18.2 | 15.92 |
| Total | 114.29 | 100.00 |

TABLE 6

| Sample | Dicamba salt | Glyph. salt | Cloud point (° C.) | Dicamba % (g a.e./L) | Glyphosate % (g a.e./L) | APG % | TA % | PG % | Anti-foam % | Water % |
|---|---|---|---|---|---|---|---|---|---|---|
| 1 | IPA | IPA | 55-60 | 8 (92) | 16 (184) | 13 | 12 | 5 | 0.1 | 37.78 |
| 2 | IPA | IPA | phase separation | 8 (92) | 16 (184) | 0 | 12 | 5 | 0.1 | 50.78 |
| 3 | IPA | IPA | 65-70 | 7 (79) | 14 (158) | 8 | 12 | 5 | 0.1 | 46.8 |
| 4 | IPA | IPA | 50-55 | 7 (79) | 14 (158) | 6 | 12 | 5 | 0.1 | 48.8 |
| 5 | IPA | IPA | 30-35 | 7 (79) | 14 (158) | 0 | 12 | 5 | 0.1 | 54.8 |
| 6 | IPA | IPA | 80-85 | 6.25 (70) | 12.5 (140) | 6 | 12 | 5 | 0.1 | 51.8 |
| 7 | IPA | IPA | 55-60 | 6.25 (70) | 12.5 (140) | 0 | 12 | 5 | 0.1 | 57.8 |
| 8 | IPA | K | 50-55 | 5.3 (60) | 11.6 (132) | 8 | 8 | 5 | 0.1 | 56.21 |
| 9 | IPA | K | 30 | 5.3 (60) | 11.6 (132) | 0 | 8 | 5 | 0.1 | 64.21 |
| 10 | DGA | K | 50-55 | 5.3 (60) | 11.6 (132) | 8 | 8 | 5 | 0.1 | 55.2 |
| 11 | DGA | K | phase separation | 5.3 (60) | 11.6 (132) | 0 | 8 | 5 | 0.1 | 63.2 |

These examples clearly illustrate that the addition of alkylpolyglucoside allows commercially acceptable cloud points to be achieved even as the total % of active ingredient loading increases. Phase separation in these examples means that two discrete liquid layers were clearly visible (one on top of the other) when the product was allowed to sit at 25° C. without agitation for >24 hrs.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

Numerous characteristics and advantages have been set forth in the foregoing description, together with details of structure and function. The novel features are pointed out in the appended claims. The disclosure, however, is illustrative only, and changes may be made in detail, especially in matters of shape, size, and arrangement of parts, within the principle of the invention, to the full extent indicated by the broad general meaning of the terms in which the general claims are expressed.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Applicants typically account for such variation by using the term "about" to modify a particular number or range. Moreover, all ranges disclosed herein are to be understood to encompass any and all subranges subsumed therein, and every number between the end points. For example, a stated range of "1 to 10 g/L" or should be considered to include any and all subranges between (and inclusive of) the minimum value of 1 g/L and the maximum value of 10 g/L; that is, all subranges beginning with a minimum value of 1 g/L or more, e.g. 1 g/L to 6.1 g/L, and ending with a maximum value of 10 g/L or less, e.g., 5.5 g/L to 10 g/L, as well as all ranges beginning and ending within the end points, e.g. 2 to 9 g/L, 3 to 8 g/L, 3 to 9 g/L, 4 to 7 g/L, and finally to each number 1 g/L, 2 g/L, 3 g/L, 4 g/L, 5 g/L, 6 g/L, 7 g/L, 8 g/L, 9 g/L and 10 g/L contained within the range.

It is further noted that, as used in this specification, the singular forms "a," "an," and "the" include plural referents unless expressly and unequivocally limited to one referent.

Further, limitations of the various embodiments of the invention are not intended to be mutually exclusive, and are considered interchangeable unless otherwise noted.

What is claimed is:

1. A compatibilized aqueous pesticidal formulation comprising:
   about 30 to about 300 g/L of at least one alkyl polyglycoside (APG); and
   about 85 to about 600 g a.e./L of an electrolytic pesticide mixture (EPM) comprising at least:
      glyphosate in a first salt form, and
      a second herbicide selected from dicamba and fomesafen in a second salt form, wherein said first salt form is different from said second salt form.

2. The compatibilized formulation of claim 1, further comprising about 1% to about 15%, by weight/volume %, of at least one hydrotrope chosen from a salt of xylene sulphonic acid, a salt of cumene sulphonic acid, and a salt of toluene sulphonic acid.

3. A method of inhibiting at least one pest in a crop area, the method comprising applying a formulation according to claim 1 to the crop area.

4. The method of claim 3, further including diluting the formulation prior to applying.

5. A method of forming the compatibilized aqueous pesticidal formulation of claim 1, the method comprising adding to a volume of water:
   about 30 to about 300 g/L of at least one alkyl polyglycoside (APG); and
   about 85 to about 600 g a.e./L of an electrolytic pesticide mixture (EPM) comprising at least the glyphosate and the second herbicide.

6. The method of claim 5, the method comprising adding to a volume of water:
   about 30 to about 300 g/L of at least one alkyl polyglycoside (APG);
   about 75 to about 500 g a.e./L of the glyphosate; and
   about 10 to about 400 g a.e./L of the second herbicide.

7. The compatibilized formulation of claim 1, wherein said formulation comprises from about 250 to about 600 g a.e./L of said electrolytic pesticide mixture (EPM).

8. A compatibilized aqueous pesticidal formulation comprising:
   about 30 to about 300 g/L of at least one alkyl polyglycoside (APG);
   about 200 to about 600 g a.e./L of an electrolytic pesticide mixture (EPM) comprising at least:
      glyphosate in a first salt form and
      a second herbicide selected from dicamba and fomesafen in a second salt form, said first salt form being different from said second salt form; and
   about 1% to about 15%, by weight/volume %, of at least one hydrotrope chosen from a salt of xylene sulphonic acid, a salt of cumene sulphonic acid, and a salt of toluene sulphonic acid.

9. The formulation of claim 1, wherein the second herbicide is dicamba and the second salt form is a diglycoamine salt.

10. The formulation of claim 1, wherein the second herbicide is fomesafen and the second salt form is a sodium salt.

11. The formulation of claim 9, where the first salt form is a potassium salt.

12. The formulation of claim 10, where in the first salt form is a potassium salt.

13. The formulation of claim 1, wherein the glyphosate and the second herbicide are present at a glyphosate:second herbicide ratio of from about 9:1 to about 1:3.

14. The formulation of claim 1, wherein the glyphosate and the second herbicide are present at a glyphosate:second herbicide ratio of from about 3:1 to about 1:3.

15. The formulation of claim 8, wherein the second herbicide is dicamba and the second salt form is a diglycoamine salt.

16. The formulation of claim 15, wherein the first salt form is a potassium salt.

17. The formulation of claim 8, wherein the second herbicide is fomesafen and the second salt form is a sodium salt.

18. The formulation of claim 17, wherein the first salt form is a potassium salt.

* * * * *